United States Patent
Luo et al.

(10) Patent No.: US 10,844,005 B1
(45) Date of Patent: Nov. 24, 2020

(54) METHOD FOR PREPARING AN N-CYCLOPROPYLMETHYL ANILINE COMPOUND

(71) Applicant: Chang Sha Jia Qiao Biotech CO., LTD., Hunan Province (CN)

(72) Inventors: Liangming Luo, Hunan Province (CN); Chaoqun Huang, Hunan Province (CN); Jintao Zhu, Hunan Province (CN); Zheng Luo, Hunan Province (CN); Rong Zhang, Hunan Province (CN)

(73) Assignee: CHANG SHA JIA QIAO BIOTECH CO., LTD., Hunan Province (CN)

( * ) Notice: Subject to any disclaimer, the term of this patent is extended or adjusted under 35 U.S.C. 154(b) by 0 days.

(21) Appl. No.: 16/837,419

(22) Filed: Apr. 1, 2020

(30) Foreign Application Priority Data

Oct. 25, 2019 (CN) .......................... 2019 1 1024148

(51) Int. Cl.
  *C07C 231/12* (2006.01)
  *C07C 67/317* (2006.01)
  *C07C 67/343* (2006.01)
(52) U.S. Cl.
  CPC .......... *C07C 231/12* (2013.01); *C07C 67/317* (2013.01); *C07C 67/343* (2013.01)

(58) Field of Classification Search
  None
  See application file for complete search history.

(56) References Cited

U.S. PATENT DOCUMENTS

2006/0241296 A1* 10/2006 Doherty ............... C07D 405/14
   544/295
2020/0178525 A1* 6/2020 Lv ......................... C07C 233/88

FOREIGN PATENT DOCUMENTS

WO   WO-2015051713 A1 * 4/2015 ......... A61K 31/5377

OTHER PUBLICATIONS

Machine generated translation of WO2015051713 (Year: 2015).*

* cited by examiner

*Primary Examiner* — Amy C Bonaparte
(74) *Attorney, Agent, or Firm* — Barnes & Thornburg LLP; Jeffrey R. Stomne

(57) ABSTRACT

Provided is a method for preparing an N-cyclopropylmethyl aniline compound, which comprises reacting a compound represented by Formula IV with cyclopropyl formaldehyde in the presence of metal zinc and an acid to generate an N-cyclopropylmethyl aniline compound represented by Formula I. The method of the present disclosure has mild reaction conditions, short reaction time, a high yield, simple processes, simple operations and low costs, and is more applicable to industrial production.

20 Claims, No Drawings

METHOD FOR PREPARING AN N-CYCLOPROPYLMETHYL ANILINE COMPOUND

The present disclosure claims the benefit of Chinese Application No. 201911024148.8 filed on Oct. 25, 2019 to the China National Intellectual Property Administration, the entire content of which is incorporated herein by reference.

TECHNICAL FIELD

The present disclosure belongs to the field of fine chemical engineering, and relates to a method for preparing an N-cyclopropylmethyl aniline compound.

BACKGROUND

N-cyclopropylmethyl aniline is an important intermediate for preparing an m-diamide compound, and is a compound having the following General Formula I:

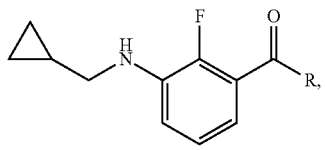

wherein R is alkyloxy or substituted aniline group (i.e.,

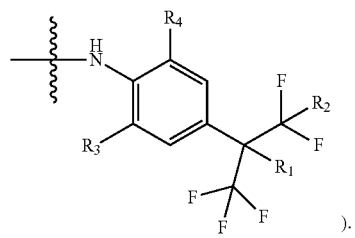

).

CN109497062 discloses a method in which bromomethyl cyclopropane reacts with a compound represented by Formula II to obtain N-cyclopropylmethyl aniline compound A according to the following scheme:

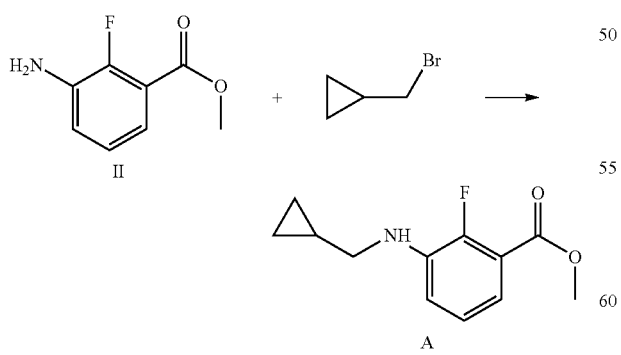

This method takes long reaction e (16 h), and has a low yield (49%) and complicated post-treatment.

CN110028423 discloses a method in which a boron reagent and cyclopropyl formaldehyde react with a compound represented by Formula III in the presence of trifluoroacetic acid to prepare N-cyclopropylmethyl aniline compound B according to the following scheme:

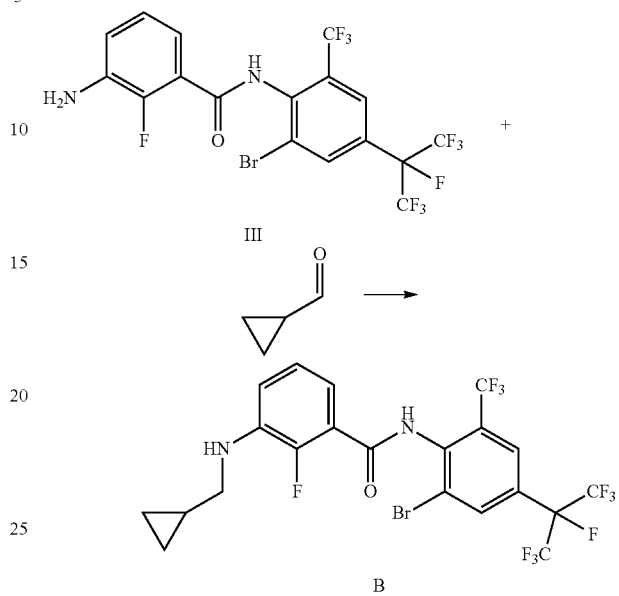

The boron reagent (sodium triacetoxyborohydride) and the trifluoroacetic acid are expensive. A large number of di-substituted compound is produced during the reaction. The yield is low.

Therefore, in the art, it is desired to develop a method for preparing an N-cyclopropylmethyl aniline compound with mild reaction conditions, a fast reaction speed, low cost and a high yield.

SUMMARY

To overcome the disadvantages of the existing arts, the present disclosure aims to provide a method for preparing an IV-cyclopropylmethyl aniline compound. The preparation method of the present disclosure has mild reaction conditions, short reaction time, a high yield, simple process, simple operation and low cost, and is more applicable to industrial production.

To achieve this object, the present disclosure adopts the technical embodiments described below.

The present disclosure provides a method for preparing an N-cyclopropylmethyl aniline compound, which comprises reacting a compound represented by Formula IV with cyclopropyl formaldehyde in the presence of metal zinc and an acid to generate an N-cyclopropylmethyl aniline compound represented by Formula I according to the following scheme:

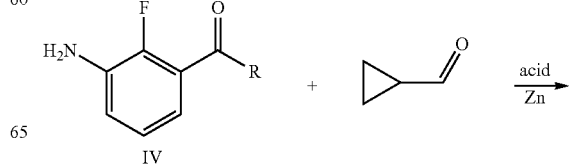

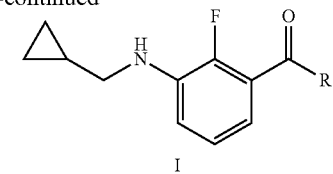

R is alkyloxy or

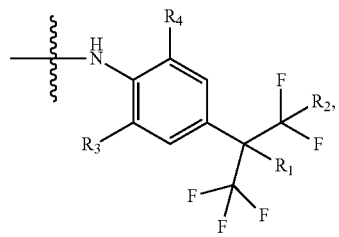

wherein $R_1$ is methoxy or fluorine, $R_2$ is fluorine or trifluoromethyl, $R_3$ is any one of H, fluorine, chlorine, bromine, iodine, nitro or trifluoromethyl, and $R_4$ is any one of trifluoromethyl, trifluoromethoxy or difluoromethoxy; and the wavy line represents the position at which the group is attached.

In the present disclosure, not only the reaction speed of the compound represented by Formula IV and cyclopropyl formaldehyde in the presence of an acid and metal zinc is accelerated, but also the reaction yield is increased. In addition, the raw materials such as the metal zinc and the acid are relatively cheap, which reduces reaction cost. Moreover, the process is facile and the operation is simple, which make it applicable to industrial production.

The preparation method of the present disclosure delivers fewer impurities, so that a high yield of products is achieved. A product with a high purity may be obtained by simple post-treatment instead of performing complicated and lengthy post-treatment.

In the present disclosure, as a preferred technical embodiment, in Formula I, R is C1-C6 alkyloxy (for example, C1, C2, C3, C4, C5 or C6 alkyloxy).

In the present disclosure, as a preferred technical embodiment, R of Formula I is methoxy, ethoxy, propoxy or isopropoxy.

In the present disclosure, as a preferred technical embodiment, R of Formula I is

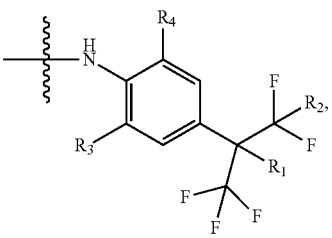

wherein $R_1$ is fluorine, $R_2$ is fluorine, $R_3$ is any one of H, bromine or iodine, and $R_4$ is any one of trifluoromethyl, trifluoromethoxy or difluoromethoxy.

In the present disclosure, the metal zinc may be zinc powder or a metal zinc bulk, preferably zinc powder.

Preferably, the acid is an inorganic acid or an organic acid. The preferred acid is formic acid, acetic acid, hydrochloric acid or sulfuric acid.

Preferably, the molar ratio of the compound represented by Formula IV to the cyclopropyl formaldehyde is 1:(1-3), for example, 1:1, 1:1.3, 1:1.5, 1:1.8, 1:2, 1:2.5, 1:2.8, 1:3 or the like.

Preferably, the molar ratio of the compound represented by Formula IV to the metal zinc is 1:(1-4), for example, 1:1, 1:1.3, 1:1.5, 1:1.8, 1:2, 1:2.5, 1:2.8, 1:3, 1:3.3, 1:3.8, 1:4 or the like.

Preferably, the molar ratio of the compound represented by Formula IV to the acid is 1:(1-4), for example, 1:1, 1:1.3, 1:1.5, 1:1.8, 1:2, 1:2.5, 1:2.8, 1:3, 1:3.3, 1:3.8, 1:4 or the like.

Preferably, the reaction is carried out in a solvent which is any one of an alcohol solvent, an ester solvent, an ether solvent or a halogenated hydrocarbon solvent.

Preferably, the alcohol solvent is any one or a combination of at least two selected from the group consisting of methanol, ethanol and isopropanol.

Preferably, the ester solvent is ethyl acetate and/or butyl acetate;

Preferably, the ether solvent is any one or a combination of at least two selected from the group consisting of diethyl ether, methyl tert-butyl ether and tetrahydrofuran.

Preferably, the halogenated hydrocarbon solvent is dichloromethane and/or di chloroethane.

Preferably, the mass ratio of the compound represented by Formula IV to the solvent is 1:(2-8), for example, 1:2, 1:2.5, 1:2.8, 1:3, 1:3.3, 1:3.8, 1:4, 1:4.5, 1:5, 1:5.5, 1:5.8, 1:6, 1:6.5, 1:7, 1:7.5, 1:8 or the like.

Preferably, the reaction is carried out at a temperature of 35° C. to 80° C., for example, 35° C., 40° C. 45° C., 50° C., 60° C., 70° C., 80° C. or the like.

Preferably, the reaction is carried out for 2 to 5 hours, for example, 2 hours, 2.5 hours, 3 hours, 3.5 hours, 4 hours, 5 hours or the like.

As a preferred technical embodiment of the present disclosure, the preparation method comprises: reacting a compound represented by Formula IV with cyclopropyl formaldehyde in a molar ratio of 1:(1-3) in the presence of metal zinc and an acid at 35° C. to 80° C. for 2 to 5 hours to obtain an N-cyclopropylmethyl aniline compound represented by Formula I, wherein the molar ratio of the compound represented by Formula IV to the metal zinc is 1:(1-4), and the molar ratio of the compound represented by Formula IV to the acid is 1:(1-4).

Compared with the existing arts, the present disclosure has the following beneficial effects:

In the present disclosure, by reacting raw materials, i.e., the compound represented by Formula. IV and cyclopropyl formaldehyde, in an acid system containing metal zinc, the speed of the reaction is increased, and a reaction yield of up to 82% and a product purity of up to 97% are achieved. Moreover, the raw materials are cheap, which reduces the reaction costs, and the reaction requires simple processes and simple operations, and is applicable to industrial production.

DETAILED DESCRIPTION

The technical embodiments of the present disclosure are further described below through specific embodiments. Those skilled in the art should understand that the embodiments are merely used to help understand the present disclosure and should not be regarded as specific limitations on the present disclosure.

Example 1

In this Example, 3-[(cyclopropylmethyl)amino]-2-fluoro-N-[4-[1,2,2,2-tetrafluoro-1-(trifluoromethyl)ethyl]-2-(trifluoromethyl)phenyl]benzamide was prepared according to the following reaction scheme:

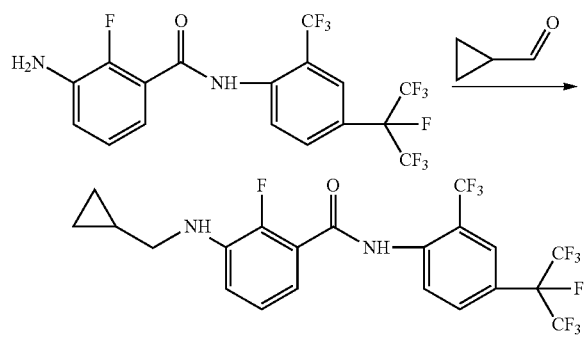

To a reaction flask equipped with a mechanical stirrer and a thermometer 47.1 g (0.1 mol) of 3-amino-2-fluoro-N-[4-[1,2,2,2-tetrafluoro-1-(trifluoromethyl)ethyl]-2-(trifluoromethyl)phenyl]benzamide, 14.0 g (0.2 mol) of cyclopropyl formaldehyde, 150 g of ethyl acetate and 13.0 g (0.2 mol) of zinc powder were sequentially added, followed by dropwise addition of 12 g (0.2 mol) of acetic acid at 60° C. After the dropwise addition was finished, the mixture was stirred for 3 hours. After the reaction was finished, the mixture was filtered. The filter cake was rinsed with 20 g of ethyl acetate. The filtrate was desolventized under reduced pressure and dried to obtain 51.2 g of 3-[(cyclopropylmethyl)amino]-2-fluoro-N-[4-[1,2,2,2-tetrafluoro-1-(trifluoromethyl)ethyl]-2-(trifluoromethyl)phenyl]benzamide in purity 98.7% and yield 97.2%.

Characterization data:
LC/MS [M+1]: m/z=521.
1H NMR (400 MHz, DMSO-d6) data (δ[ppm]): 10.18 (s, 1H), 8.12-8.07 (m, 1H), 8.04 (d, J=8.7 Hz, 1H), 7.92 (s, 1H), 7.10 (t, J=7.9 Hz, 1H), 6.94 (t, J=8.2 Hz, 1H), 6.90-6.82 (m, 1H), 5.82-5.72 (m, 1H), 3.03 (t, J=6.2 Hz, 2H), 1.12-1.08 (m, 1H), 0.50-0.42 (m, 2H), 0.24 (q, J=4.4 Hz, 2H).

Example 2

In this Example, methyl 3-[(cyclopropylmethyl)amino]-2-fluorobenzoate was prepared according to the following reaction scheme:

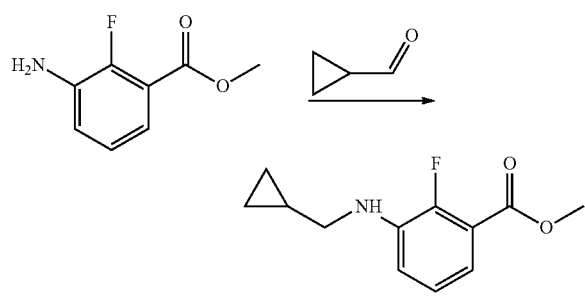

To a reaction flask equipped with a mechanical stirrer and a thermometer 17.1 g (0.1 mol) of methyl 3-amino-2-fluorobenzoate, 21.0 g (0.3 mol) of cyclopropyl formaldehyde, 136 g of methanol and 26.0 g (0.4 mol) of zinc powder were sequentially added, followed by dropwise addition of 24 g (0.4 mol) of acetic acid at 40° C. After the dropwise addition was finished, the mixture was stirred for 5 hours. After the reaction was finished, the reaction solution was filtered. The filter cake was rinsed with 20 g of methanol. The filtrate was desolventized under reduced pressure and dried to obtain 21.5 g of methyl 3-[(cyclopropylmethyl)amino]-2-fluorobenzoate in purity 98.5% and yield 95.0%.

Characterization data:
LC/MS [M±1]: m/z=224.
1H NMR (400 MHz, CDCl₃) data (δ[ppm]): 7.18-7.15 (m, 1H), 7.05-7.01 (m, 1H), 6.85-6.82 (m, 1H), 4.21 (br s, 1H), 3.93 (s, 3H), 3.01 (d, J=5.6 Hz, 2H), 1.15-1.12 (m, 1H), 0.62-0.58 (m, 2H), 0.30-0.25 (m, 2H).

Example 3

In this Example, ethyl 3-[(cyclopropylmethyl)amino]-2-fluorobenzoate was prepared according to the following reaction scheme:

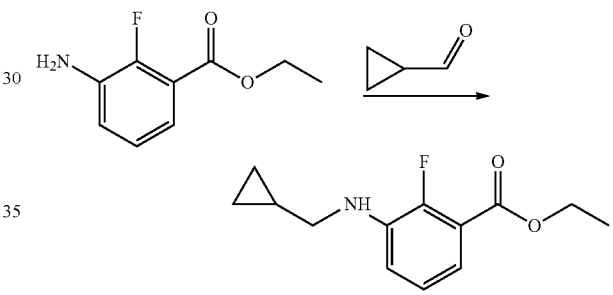

To a reaction flask equipped with a mechanical stirrer and a thermometer 18.5 g (0.1 mol) of ethyl 3-amino-2-fluorobenzoate, 21.0 g (0.3 mol) of cyclopropyl formaldehyde, 74 g of ethanol and 19.5 g (0.3 mol) of zinc powder were sequentially added, followed by dropwise addition of 30.4 g (0.3 mol) of hydrochloric acid at 60° C. After the dropwise addition was finished, the mixture was stirred for 3 hours, After the reaction was finished, the reaction solution was filtered. The filter cake was rinsed with 20 g of ethanol. The filtrate was desolventized under reduced pressure and dried to obtain 21.6 g of ethyl 3-[(cyclopropylmethyl)amino]-2-fluorobenzoate in purity 98.0% and yield 89.3%.

Characterization data: LC/MS [M+1]: m/z=238.

Example 4

In this Example, propyl 3-[(cyclopropylmethyl)amino]-fluorobenzoate was prepared according to the following reaction scheme:

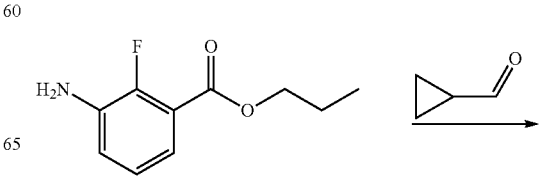

-continued

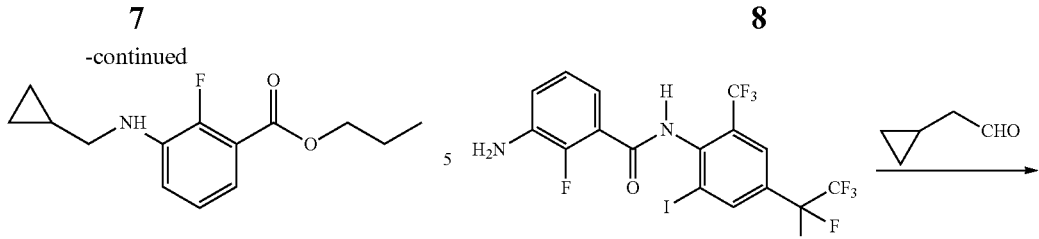

To a reaction flask equipped with a mechanical stirrer and a thermometer 19.9 g (0.1 mol) of propyl 3-amino-2-fluoro-benzoate, 14 g (0.2 mol) of cyclopropyl formaldehyde, 60 g of diethyl ether and 13 g (0.2 mol) of zinc powder were sequentially added, followed by dropwise addition of 24 g (0.4 mol) of acetic acid at 35° C. After the dropwise addition was finished, the mixture was stirred for 5 hours. After the reaction was finished, the reaction solution was filtered. The filter cake was rinsed with 20 g of diethyl ether. The filtrate was desolventized under reduced pressure and dried to obtain 21.2 g of propyl 3-[(cyclopropylmethyl)amino]-2-fluorobenzoate in purity 97.3% and yield 82.2%.

Characterization data: LC/MS [M+1]: m/z=252.

Example 5

In this Example, isopropyl 3-[(cyclopropylmethyl)amino]-2-fluorobenzoate was prepared according to the following reaction scheme:

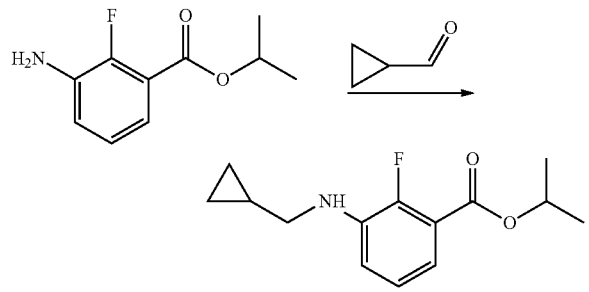

To a reaction flask equipped with a mechanical stirrer and a thermometer 19.9 g (0.1 mol) of isopropyl 3-amino-2-fluoro-benzoate, 21.0 g (0.3 mot) of cyclopropyl formaldehyde, 80 g of isopropanol and 19.5 g (0.3 mol) of zinc powder were sequentially added, followed by dropwise addition of 18 g (0.3 mol) of acetic acid at 60° C. After the dropwise addition was finished, the mixture was stirred for 3 hours. After the reaction was finished, the reaction solution was filtered. The filter cake was rinsed with 20 g of isopropanol. The filtrate was desolventized under reduced pressure and dried to obtain 22.0 g of isopropyl 3-[(cyclopropylmethyl)amino]-2-fluorobenzoate in purity 97.6% and yield 85.5%.

Characterization data: LC/MS. [M+1]: m/z=252.

Example 6

In this Example, 3-[(cyclopropylmethyl)amino]-N-[2-iodo-4-[1,1,1,2,3,3-heptafluoroprop-2-yl]-6-(trifluoromethyl)phenyl]benzamide was prepared according to the following reaction scheme:

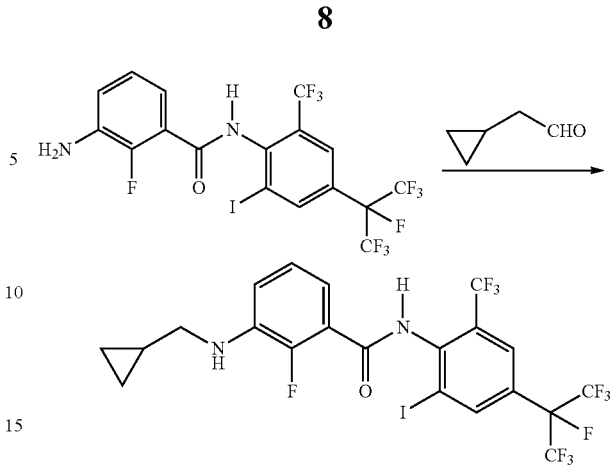

To a reaction flask equipped with a mechanical stirrer and a thermometer 29.6 g (0.05 mol) of 3-amino-2-fluoro-N-[2-iodo-4-[1,1,1,2,3,3-heptafluoroprop-2-yl]-6-(trifluoromethyl)phenyl]benzamide, 10.5 g (0.15 mol) of cyclopropyl formaldehyde, 48.8 g of dichloromethane and 13 g (0.2 mol) of zinc powder were sequentially added, followed by dropwise addition of 10.0 g (0.1 mol) of sulfuric acid at 40° C. After the dropwise addition was finished, the mixture was stirred for 5 hours. After the reaction was finished, the reaction solution was filtered. The filter cake was rinsed with 10 g of dichloromethane. The filtrate was desolventized under reduced pressure, diluted with 50 ml of water, adjusted with 30% sodium hydroxide to pH 8~9, cooled to 0° C., filtered and dried to obtain 29.4 g of 3-[(cyclopropylmethyl)amino]-N-[2-iodo-4-[1,1,1,2,3,3-heptafluoroprop-2-yl]-6-(trifluoromethyl)phenyl]-2-fluorobenzamide in purity 98.3% and yield 89.5%.

Characterization data:
LC/MS [M+1]: m/z=647.
1H NMR (400 MHz, DMSO-d6) data (δ[ppm]): 10.53 (s, 1H), 8.41 (s, 1H) 7.97 (s, 1H), 7.11 (m, 1H), 6.96-6.91 (m, 1H), 6.84-6.81 (m, 1H), 5.79-5.75 (m, 1H), 3.04 (t, J=6.2 Hz, 2H), 1.15-1.07 (m, 1H), 0.49-0.44 (m, 2H), 0.28-0.24 (m, 2H).

Example 7

In this Example, 3-[(cyclopropylmethyl)amino]-N-[2-bromo-4-[1,1,1,2,3,3,3-heptafluoroprop-2-yl]-6-(difluoromethoxy)phenyl]-2-fluorobenzamide was prepared according to the following reaction scheme:

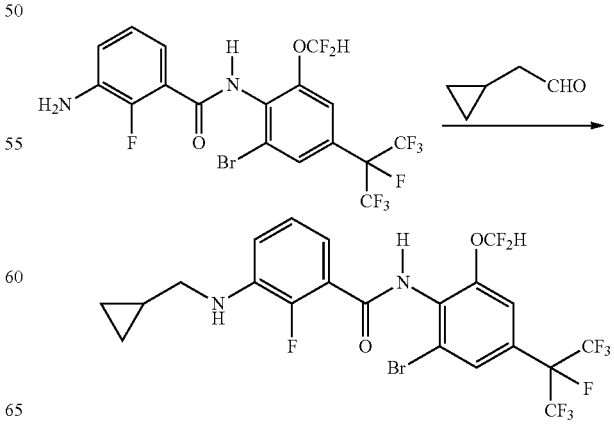

To a reaction flask equipped with a mechanical stirrer and a thermometer 27.2 g (0.05 mol) of 3-amino-N-[2-chloro-4-[1,1,1,2,3,3,3-heptafluoroprop-2-yl]-6-(difluoromethoxy)phenyl]-2-fluorobenzamide, 7 g (0.1 mol) of cyclopropyl formaldehyde, 75 g of dichloroethane and 3.3 g (0.05 mol) of zinc powder were sequentially added, followed by dropwise addition of 3 g (0.05 mol) of acetic acid at 80° C. After the dropwise addition was finished, the mixture was stirred for 2 hours. After the reaction was finished, the reaction solution was filtered. The filter cake was rinsed with 10 g of dichloroethane. The filtrate was desolventized under reduced pressure, diluted with 25 ml of water, adjusted with 30% sodium hydroxide to pH 8~9, cooled to 0° C., filtered and dried to obtain 27.6 g of 3-[(cyclopropylmethyl)amino]-N-[2-bromo-4-[1,1,1,2,3,3,3-heptafluoroprop-2-yl]-6-(difluoromethoxy)phenyl]-2-fluorobenzamide in purity 98.1% and yield 90.6%.

Characterization data:

LC/MS [M+1]: m/z=598.

1H NMR (400 MHz, DMSO-d6) data (δ[ppm]): $^1$H NMR (400 MHz, DMSO-d6) 10.01 (s, 1H), 7.66 (s, 1H), 7.30 (s, 1H), 7.09 (t, J=72.0 Hz, 1H), 6.85 (t, J=7.8 Hz, 1H), 6.69 (t, J=7.7 Hz, 1H), 6.56 (t, J=6.2 Hz, 1H), 5.47 (s, 1H), 2.79 (t, J=5.7 Hz, 2H), 0.90-0.80 (m, 1H), 0.24-0.18 (m, 2H), 0.01 (q, J=4.9 Hz, 2H).

Example 8

In this Example, 3-[(cyclopropylmethyl)amino]-N-[2-bromo-4-[1,1,1,2,3,3,3-heptafluoroprop-2-yl]-6-(trifluoromethyl)phenyl]-2-fluorobenzamide was prepared according to the following reaction scheme:

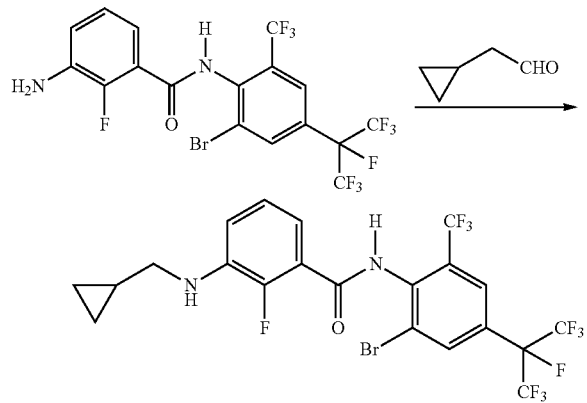

To a reaction flask equipped with a mechanical stirrer and a thermometer 27.3 g (0.05 mol) of 3-amino-N-[2-bromo-4-[1,1,1,2,3,3,3-heptafluoroprop-2-yl]-6-(trifluoromethyl)phenyl]-2-fluorobenzamide, 7 g (0.1 mop of cyclopropyl formaldehyde, 75 g of isopropanol and 3.3 g (0.05 mol) of zinc powder were sequentially added, followed by dropwise addition of 10.2 g (0.1 mol) of hydrochloric acid at 60° C. After the dropwise addition was finished, the mixture was stirred for 3 hours. After the reaction was finished, the reaction solution was filtered. The filter cake was rinsed with 10 g of isopropanol. The filtrate was desolventized under reduced pressure and dried to obtain 7.7.2 g of 3-[(cyclopropylmethyl)amino]-N-[2-bromo-4-[1,1,1,2,3,3,3-heptafluoroprop-2-yl]-6-(trifluoromethyl)phenyl]-2-fluorobenzamide in purity 97.8% and yield 88.8%.

Characterization data:

LC/MS [M+1]: m/z=600.

1H NMR (400 MHz, DMSO-d6) data (δ[ppm]): 10.54 (s, 1H), 8.42 (s, 1H), 7.96 (s, 1H), 7.10 (t, J=8.0 Hz, 1H), 6.96-6.91 (m, 1H), 6.83-6.79 (m, 1H), 5.79-5.75 (m, 1H) 3.03 (t, J=6.2 Hz, 2H), 1.14-1.05 (m, 1H), 0.48-0.43 (m, 2H), 0.29-0.2 (m, 2H).

Example 9

In this Example, 3-[(cyclopropylmethyl)amino]-N-[2-bromo-4-[1,1,1,2,3,3,3-heptafluoroprop-2-yl]-6-(trifluoromethoxy)phenyl]-2-fluorobenzamide was prepared according to the following reaction scheme:

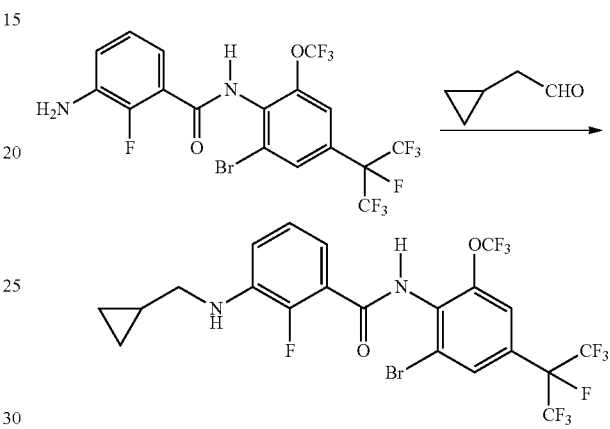

To a reaction flask equipped with a mechanical stirrer and a thermometer 28.05 g (0.05 mol) of 3-amino-N-[2-bromo-4-[1,1,1,2,3,3,3-heptafluoroprop-2-yl]-6-(trifluoromethoxy)phenyl]-2-fluorobenzamide, 7 g (0.05 mol) of cyclopropyl formaldehyde, 60 g of butyl acetate and 6.5 g (0.1 mol) of zinc powder were sequentially added, followed by dropwise addition of 5.2 g (0.1 mol) of formic acid at 80° C. After the dropwise addition was finished, the mixture was stirred for 2 hours. After the reaction was finished, the reaction solution was filtered. The filter cake was rinsed with 20 g of butyl acetate. The filtrate was desolventized under reduced pressure and dried to obtain 26.0 of 3-[(cyclopropylmethyl)amino]-N-[2-bromo-4-[1,1,1,2,3,3,3-heptafluoroprop-2-yl]-6-(trifluoromethoxy)phenyl]-2-fluorobenzamide in purity 97.0% and yield 82.0%.

Characterization data:

LC/MS [M+1]: m/z=616.

1H NMR (400 MHz, DMSO-d6) data (δ[ppm]): 10.53 (s, 1H), 8.10 (s, 1H), 7.78 (s, 1H), 7.13-7.07 (m, 1H), 6.96-6.91 (m, 1H), 6.78-6.75 (m, 1H), 5.78-5.74 (m, 1H), 3.03 (t, J=6.2 Hz, 2H), 0.98-0.90 (m, 1H), 0.26-0.22 (m, 2H), 0.16-0.12 (m, 2H).

Example 10

In this Example, 3-[(cyclopropylmethyl)amino]-2-fluoro-N-[2-nitro-4-[1,2,2,2-tetrafluoro-1-(trifluoromethyl)ethyl]-6-(trifluoromethyl)phenyl]benzamide was prepared according to the following reaction scheme:

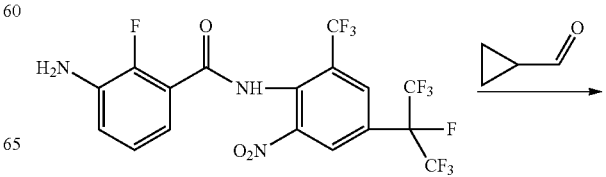

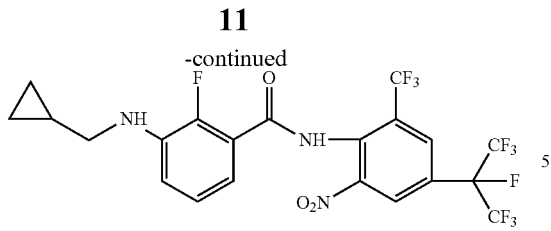

To a reaction flask equipped with a mechanical stirrer and a thermometer 25.8 g (0.05 mol) of 3-amino-2-fluoro-N-[2-nitro-4-[1,2,2,2-tetrafluoro-1-(trifluoromethyl)ethyl]-6-(trifluoromethyl)phenyl]benzamide, 7.0 g (0.1 mol) of cyclopropyl formaldehyde, 103 g of tetrahydrofuran, and 6.5 g (0.1 mol) of zinc powder were sequentially added, followed by dropwise addition of 10.5 g (0.2 mol) of formic acid at 60° C. After the dropwise addition was finished, the mixture was stirred for 3 hours. After the reaction was finished, the reaction solution was filtered. The filter cake was rinsed with 10 g of tetrahydrofuran. The filtrate was desolventized under reduced pressure and dried to obtain 25.4 g of 3-[(cyclopropylmethyl)amino]-2-fluoro-N-[2-nitro-4-[1,2,2,2-tetrafluoro-1-(trifluoromethyl)ethyl]-6-(trifluoromethyl)phenyl]benzamide in purity 98.1% and yield 88.2%.

Characterization data:

LC/MS [M+1]: m/z=566.

1H NMR (400 MHz, DMSO-d6) data (δ[ppm]): 10.53 (s, 1H), 8.45 (s, 1H), 8.02 (s, 1H), 7.12 (t, J=8.0 Hz, 1H), 6.97-6.93 (m, 1H), 6.86-6.80 (m, 1H), 5.78-5.75 (m, 1H), 3.05 (m, 2H), 1.16-1.09 (m, 1H), 0.49-0.43 (m, 2H), 0.30-0.24 (m, 2H).

Example 11

In this Example, 3-[(cyclopropylmethyl)amino]-2-fluoro-N-[4-[1,2,2,2-tetrafluoro-1-(trifluoromethyl)ethyl]-2,6-bis(trifluoromethyl)phenyl]benzamide was prepared according to the following reaction scheme:

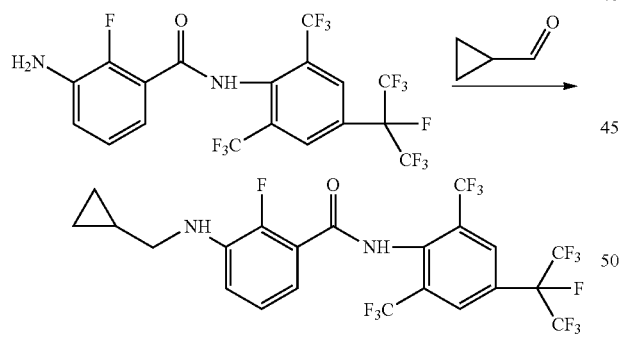

To a reaction flask equipped with a mechanical stirrer and a thermometer 27.0 g (0.05 mol) of 3-amino-2-fluoro-N-[4-[1,2,2,2-tetrafluoro-1-(trifluoromethyl)ethyl]-2,6-bis(trifluoromethyl)phenyl]benzamide, 10.5 g (0.15 mol) of cyclopropyl formaldehyde, 135 g of methyl tert-butyl ether and 13.0 g (0.2 mol) of zinc powder were sequentially added, followed by dropwise addition of 12 g (0.2 mol) of acetic acid at 60° C. After the dropwise addition was finished, the mixture was stirred for 3 hours. After the reaction was finished, the reaction solution was filtered. The filter cake was rinsed with 10 g of methyl tert-butyl ether. The filtrate was desolventized under reduced pressure and dried to obtain 26.5 g of 3-[(cyclopropylmethyl)amino]-2-fluoro-N-[4-[1,2,2,2-tetrafluoro-1-(trifluoromethyl)ethyl]-2,6-bis(trifluoromethyl)phenyl]benzamide in purity 97.6% and yield 88.0%.

Characterization data:

LC/MS [M±1]: m/z=589.

1H NMR (400 MHz, DMSO-d6) data (δ[ppm]): 10.55 (s, 1H), 8.43 (s, 1H), 8.06 (s, 1H), 7.14 (t, J=8.0 Hz, 1H), 6.99-6.95 (m, 1H), 6.86-6.81 (m, 1H) 5.79-5.75 (m, 1H), 3.06 (m, 2H), 1.17-1.11 (m, 1H), 0.48-0.42 (m, 2H), 0.31-0.24 (m, 2H).

The applicant has stated that although the preparation method for the N-cyclopropylmethyl aniline compound of the present disclosure is described through the embodiments described above, the present disclosure is not limited to the embodiments described above, which means that implementation of the present disclosure does not necessarily depend on the embodiments described above. It should be apparent to those skilled in the art that any improvements made to the present disclosure, and equivalent replacements of various raw materials, the addition of adjuvant ingredients and the selection of specific manners, etc. in the present disclosure all fall within the protection scope and the disclosure scope of the present disclosure.

What is claimed is:

1. A method for preparing an N-cyclopropylmethyl aniline compound, comprising reacting a compound represented by Formula IV with cyclopropyl formaldehyde in the presence of metal zinc and an acid to generate an N-cyclopropylmethyl aniline compound represented by Formula I according to the following scheme:

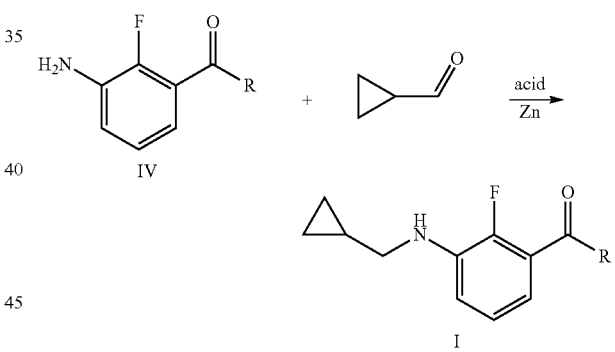

wherein R is alkyloxy or

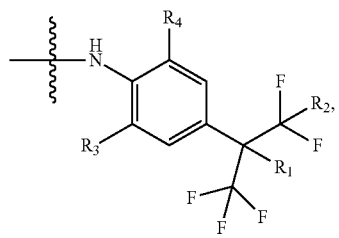

wherein $R_1$ is methoxy or fluorine, $R_2$ is fluorine or trifluoromethyl, $R_3$ is any one of H, fluorine, chlorine, bromine, iodine, nitro or trifluoromethyl, and $R_4$ is any one of trifluoromethyl, trifluoromethoxy or difluoromethoxy.

2. The method according to claim 1, wherein R is C1-C6 alkyloxy.

3. The method according to claim 2, wherein R is methoxy, ethoxy, propoxy or isopropoxy.

4. The method according to claim 1, wherein R is

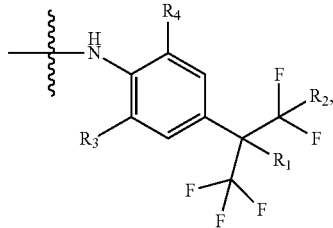

wherein $R_1$ is fluorine, $R_2$ is fluorine, $R_3$ is H, bromine or iodine, and $R_4$ is any one of trifluoromethyl, trifluoromethoxy or difluoromethoxy.

5. The method according to claim 1, wherein the metal zinc is zinc powder or a metal zinc bulk.

6. The method according to claim 5, wherein the metal zinc is zinc powder.

7. The method according to claim 1, wherein the acid is an inorganic acid or an organic acid.

8. The method according to claim 7, wherein the acid is formic acid, acetic acid, hydrochloric acid or sulfuric acid.

9. The method according to claim 1, wherein the molar ratio of the compound represented by Formula IV to the cyclopropyl formaldehyde is 1:(1-3).

10. The method according to claim 1, wherein the molar ratio of the compound represented by Formula IV to the metal zinc is 1:(1-4).

11. The method according to claim 1, wherein the molar ratio of the compound represented by Formula IV to the acid is 1:(1-4).

12. The method according to claim 1, wherein the reaction is carried out in a solvent which is any one of an alcohol solvent, an ester solvent, an ether solvent or a halogenated hydrocarbon solvent.

13. The method according to claim 12, wherein the alcohol solvent is any one or a combination of at least two selected from the group consisting of methanol, ethanol and isopropanol.

14. The method according to claim 12, wherein the ester solvent is ethyl acetate and/or butyl acetate.

15. The method according to claim 12, wherein the ether solvent is any one or a combination of at least two selected from the group consisting of diethyl ether, methyl tert-butyl ether and tetrahydrofuran.

16. The method according to claim 12, wherein the halogenated hydrocarbon solvent is dichloromethane and/or dichloroethane.

17. The method according to claim 12, wherein the mass ratio of the compound represented by Formula IV to the solvent is 1:(2-8).

18. The method according to claim 1, wherein the reaction is carried out at a temperature of 35° C. to 80° C.

19. The method according to claim 1, wherein the reaction is carried out for 2 to 5 hours.

20. The method according to claim 1, comprising reacting a compound represented by Formula IV with cyclopropyl formaldehyde in a molar ratio of 1:(1-3) in the presence of metal zinc and an acid at 35° C. to 80° C. for 2 to 5 hours to obtain an N-cyclopropylmethyl aniline compound represented by Formula I, wherein the molar ratio of the compound represented by Formula IV to the metal zinc is 1:(1-4), and the molar ratio of the compound represented by Formula IV to the acid is 1:(1-4).

* * * * *